United States Patent [19]

Hans-Jürgen et al.

[11] 4,400,258
[45] Aug. 23, 1983

[54] MEASURING DEVICE FOR FACILITATING THE ELECTRICAL MEASUREMENT OF A SUBSTANCE

[75] Inventors: Busack Hans-Jürgen; Klaus Kaross; Helmut Rinne, all of Lübeck, Fed. Rep. of Germany

[73] Assignee: Drägerwerk Aktiengesellschaft, Fed. Rep. of Germany

[21] Appl. No.: 358,529

[22] Filed: Mar. 16, 1982

[30] Foreign Application Priority Data

Mar. 21, 1981 [DE] Fed. Rep. of Germany ....... 3111190

[51] Int. Cl.³ .............................................. G01N 27/50
[52] U.S. Cl. .................................. 204/415; 128/635
[58] Field of Search ................... 204/195 P, 195 B; 128/635

[56] References Cited

U.S. PATENT DOCUMENTS

| | | | |
|---|---|---|---|
| 3,325,378 | 6/1967 | Greene et al. | 204/195 P |
| 4,185,620 | 1/1980 | Hagihara | 204/195 B |
| 4,280,505 | 7/1981 | Dali et al. | 204/195 P |
| 4,303,076 | 12/1981 | Danek | 128/635 |
| 4,311,151 | 1/1982 | Hagihara | 204/195 P |
| 4,359,054 | 11/1982 | Leist et al. | 204/195 B |

FOREIGN PATENT DOCUMENTS 2021784 12/1979 United Kingdom ................ 128/635

*Primary Examiner*—Howard S. Williams
*Assistant Examiner*—Terry Chapman
*Attorney, Agent, or Firm*—McGlew and Tuttle

[57] ABSTRACT

A measuring device for facilitating the electro-chemical measurement of a substance such as a gas comprises a holder ring which has an opening therethrough with an inwardly extending annular resilient sealing lip extending into the opening and an end face with an inner annular projecting portion defining a fitting strip and an outer annular projecting portion spaced radially outwardly from the inner annular portion. A membrane is engaged over the opening and the inner annular projecting portion and its periphery rests in a space between the inner and outer projecting portions. A tightening ring is engaged with the hole of the ring and it includes an end face with an annular groove which is positionable over the inner annular projection of the holder ring. The tightening ring includes an inner annular counter ring part engageable over the membrane and against the sealing lip of the holder ring. It also includes an outer annular part disposed between the inner annular projecting portion and the outer annular projection of the holder ring. The groove of the tightening ring defines an electrolytic receiving space overlying the membrane. The inner annular counterring part of the tightening ring and the sealing lip of the holder ring define with the membrane a releasable seal for the electrolyte in this electrolyte sealing space. The measuring device also includes a body having a central projecting part which contains two electrodes in spaced apart insulated relationship which engage against the membrane. The projecting part deflects the sealing lip of the holding ring to release this electrolyte seal and to permit the electrolyte to flow over the membrane to the electrodes.

7 Claims, 2 Drawing Figures

MEASURING DEVICE FOR FACILITATING THE ELECTRICAL MEASUREMENT OF A SUBSTANCE

FIELD AND BACKGROUND OF THE INVENTION

This invention relates in general to measuring devices and in particular to a new and useful device for facilitating the electro-chemical measurement of a substance such as a gas.

Electro-chemical measuring devices contain, as is known, an electrode system with at least two electrodes that are connected through an electrolytic layer and which are covered against the medium to be measured by means of a membrane that can be penetrated by a gas to be measured but cannot be penetrated by the electrolytes. The sensitivity of the electro-chemical analyzers depends on the condition of this separator membrane and the electrolytes. The electrolyte system must be renewed from time to time. This is done by changing the membrane and the electrolysis. For the most part this involves working with small parts. The electrolyte must be properly portioned, and dirt cannot be permitted. The membrane may have no wrinkles, and must be positioned and attached under a specific tension. All in all, this is a difficult and time-consuming procedure that cannot reliably be done, particularly by inexperienced persons, even at the measuring site. Even the use of known clamping devices in principle makes little difference.

In a known arrangement for changing membranes and electrolyte fillings in electro-chemical analyzers, the membranes are assembled in a replaceable capsule. By means of a screw-ring the capsule is maintained in contact with the analyzer before its electrodes. A portion of one electrode overhangs the other. As delivered, the capsule consists of a cup-shaped holder having a plastic-sheet floor that curves inward. The wall and the floor of the holder are covered with the membrane. The parts on the wall are closely connected by means of reinforcing rings and tension rings. The space between them and the curved floor is filled with electrolyte. When the capsule is put on, the floor is turned toward the electrodes. When the capsule is being screwed on with the screw-ring, the floor is penetrated by the projecting portion of one electrode; the overflowing electrolyte then moistens the electrodes. Flexible rings on the analyzer and screw-ring ensure the ouside seal after tightening and also the rigidity of the membrane. A disadvantage is that the storage time of the unused capsules is limited, because the electrolyte under the broad membrane is even subject to drying out than during operation if the membrane is completely covered by the screw-ring. When the capsule is installed, before penetration occurs the curved floor is distorted; the distortions, transmitted through the electrolyte filling, can lead to uncontrolled stretching of the membrane and can change the sensitivity of measurement through changes in its qualities. The foregoing electrode makes the analyzer unsuitable for many kinds of measure. The construction of the capsule of the capsule itself, and the loose screw-ring needed in addition, along with the sealing elements, is complicated and bothersome to handle.

SUMMARY OF THE INVENTION

The invention provides an electro-chemical measuring device that offers the possibility of replacing varying membranes and electrolytes simply and without special additional equipment.

In accordance with the invention the measuring device for facilitating the electro-chemical measurement of a substance, for example, measuring the gas content of a person's blood, comprises a holder ring which has a central opening with an inwardly extending annular resilient sealing lip portion of the ring being disposed in the opening. The holder ring includes an end face with an inner annular projecting portion defining a fitting strip and an outer annular portion spaced radially outwardly from the annular projecting portion. The membrane is engaged over the opening end over the inner annular projection of the holder ring. The tightening ring has an end face with an annular groove positionable over the inner annular projection and it includes an inner annular counter ring part engageable over the membrane and against the sealing lip as well as an outer annular part disposed between the inner annular projecting portion and the outer annular projecting portion of the holder ring. The groove of the tightening ring defines an electrolyte receiving space overlying the membrane. The inner annular counter ring part and the sealing lip define with the membrane and releasable seal for the electrolyte sealing space. The seal is released by inserting a measuring device body which has a central projecting part which is engaged into the opening of the holder ring over the membrane. A pair of electrodes are arranged in the central projecting part and they are insulated from each other and engage against the membrane. When the central deflecting part is applied to the opening it deflects the sealing lip to release the seal and to permit the electrolyte to flow over the membrane to the electrodes.

The embodiment according to the invention, with construction of the membrane holder as a complete but simple structural component, proves to be very advantageous. It can be removed from the body of the measuring device without special equipment. The holder straps can be of assistance in this process. A new membrane holder, a simple and complete component that is ready for use, is then positioned on the body of the measuring device and automatically engages in a toggle-type fastener. Having been inspected at the manufacturing plant, the membrane is in any case perfectly stretched and calibrated; after the membrane holder has been positioned on the body of the measuring device the electrolyte penetrates the space between the membrane and the electrodes as needed, because its penetration is ensured. Thanks to the new membrane and the new electrolyte the function of the measuring device is restored. The holder straps provide assistance in removal of the measuring device, which is held to the membrane by means of adhesive.

The spring-loaded latch between the holder ring and the tightening ring simplifies manufacture of the membrane holder. Other methods of holding them together, e.g. adhesive, can also be used.

The holder straps on the tightening ring make it easy to position the membrane holder on, or remove the membrane holder from, the body of the measuring device. The complete measuring device can also be suspended. If the holder straps are in the way, they can be simply cut off.

Accordingly, it is an object of the invention to provide an improved device for facilitating the electrochemical measurement of a substance which includes a holder ring which is interengaged with a tightening ring. For example by a screw thread or latching engagement which clamp between them a membrane such that a electrolyte space is defined annularly around the periphery of the membrane which is opened by insertion of a central head portion of the measuring device which contains electrodes in a manner such that the electrodes are supplied with electrolytes over the membrane due to the interengagement of the measuring device body with the holder ring and counter ring.

A further object of the invention is to provide an electrochemical measuring device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention is illustrated.

DESCRIPTION OF THE PREFERRED EMBODIMENTS

Figure 1:
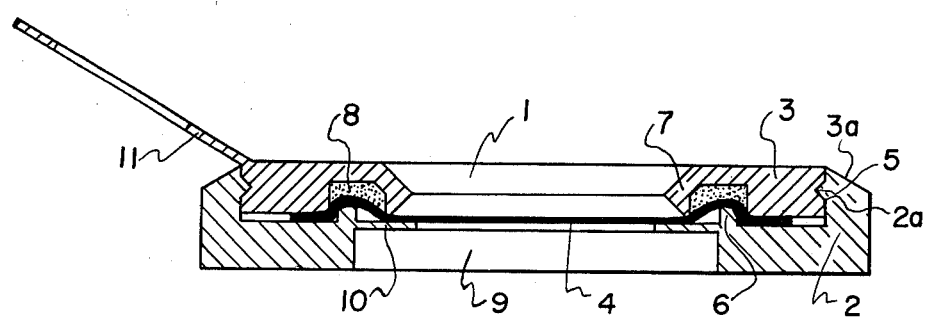
FIG. 1 is a partial section view of a device for facilitating electro-chemical measurement of a substance such as gas constructed in accordance with the invention.
Figure 2:
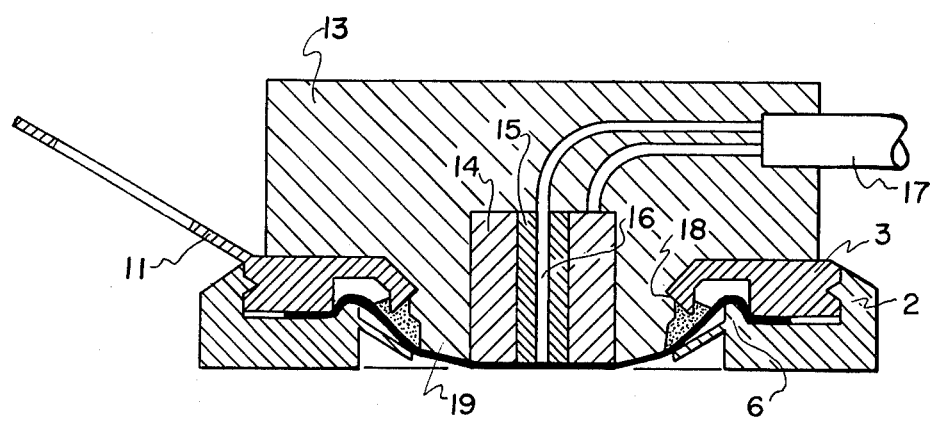
FIG. 2 is a view similar to FIG. 1 showing the device with a measuring device body having electrodes engaged therewith.

Referring to the drawings, in particular the invention embodied therein, comprises the device for facilitating the electro-chemical measurement of a substance such as a gas which is shown in FIG. 1 and which is combined with an actual measuring instrument as shown in FIG. 2. Membrane holder 1 of FIG. 1 comprises a ring-shaped holder-ring 2 and a tightening ring 3, between which the membrane 4 is stretched and held. The parts are held together by means of a spring-loaded latch 5, in the form of a threader projection 2a on holder ring 2 which engages a recess 3a of the tightening ring 3 or which may be otherwise formed between the two rings. The holder ring 2 has a tubular sleeve forming a fitting strip 6, over an end of which the membrane 4 is stretched by a counter-ring part 7 of the tightening ring 3. The counter ring part 7, define an in-turned groove or electrolyte area 8. A sealing lip part 10 of the holding ring 2 extends into a central opening 9 of the holder ring 2 and along with counter ring 7 seals the electrolyte area 8 and applies pressure on the membrane 4.

The tightening ring 3 has a holder strap 11. This holder strap 11 simplifies handling during installation or removal of the membrane holder 1 on/from a measuring device and also allows the device to be suspended after installation.

FIG. 2 shows the membrane holder 1 installed on a measuring device hvaing a housing or body 13. The body 13 of the measuring device contains a reference electrode 14 and, in the center, within insulation 15, a measuring electrode 16. Appropriate electrical connections 17 are provided for the electrodes 14 and 16.

The membrane holder 1 is held on the body 13 for a snap or threaded fastener construction 18 in such manner that the membrane 4 is stretched over the electrodes by a cylindrical projecting central portion 19 of the measuring device body 13. The cylindrical central portion 19 engages so far into the surrounding sealing lip 10 that it deflects to permit electrolyte to pass out of the electrolyte area 8 and, through capillary action, penetrates the space between the membrane 4 and the electrodes 14 and 16, and a homogeneous electrolytic layer forms between the electrodes.

The membrane holder 1 can easily be installed or removed at the measuring site by even an inexperienced person.

A measuring device for facilitating electro-chemical measurement of a substance is used for example, in measuring a gas content of a patient's blood in which case the device with the membranes is applied over the person's skin.

What is claimed is:

1. A measuring device for facilitating the electrical measurement of a substance, comprising a holder ring, having an opening, said holder ring having a wall bounding said opening with an inwardly extending annular resilient sealing lip, said holder ring also having an end face with an inner annular projecting portion defining a fitting strip and also having an outer annular projecting portion spaced radially outwardly from said inner annular projecting portion, a membrane engaged over said inner annular projection and the opening of said holder ring, a tightening ring having an end face with an annular groove is positioned over said inner annular projection and including an inner annular counter ring part engageable over said membrane and against said sealing lip and an outer annular tightening ring projecting part disposed between said inner annular projecting portion and said outer annular projecting portion of said holder ring, said groove of said tightening ring defining an electrolyte receiving space overlying said membrane, said inner annular counter ring part and sealing lip defining with said membrane a releasable seal for said electrolyte sealing space.

2. A measuring device according to claim 1, including latch means defined between said holder ring and said tightening ring for releasably interengaging said rings.

3. A measuring device according to claim 1, including a measuring device body having a central projecting part engaged in the opening of said holder ring over said membrane, first and second spaced apart electrodes located in said central projecting part and engaged over said membrane, said central projecting part deflecting said sealing lip to release said seal and to permit the electrolyte in said electrolyte sealing space to flow over said membrane to said electrodes.

4. A measuring device according to claim 3, wherein said central projecting part and said tightening ring include engageable portions defining a releasable latch between said parts.

5. A measuring device according to claim 3, wherein said electrodes includes an annular electrode and a cylindrical electrode disposed within said annular electrode and insulated therefrom.

6. A measuring device according to claim 3, wherein said tightening ring includes a central opening with a wall bounding said central opening having a projecting edge, said central part of said body including a receiving recess into which said projecting portion of said tightening ring extends.

7. A measuring device according to claim 1, including a holder strap connected to said tightening ring.

* * * * *